(12) United States Patent
Rotem et al.

(10) Patent No.: US 10,184,615 B2
(45) Date of Patent: Jan. 22, 2019

(54) PERISTALTIC INFUSION PUMP WITH LOCKING MECHANISM

(71) Applicant: Q-CORE MEDICAL LTD., Netanya (IL)

(72) Inventors: Shachar Rotem, M.P. Hefer (IL); Ori Goldor, Amikam (IL)

(73) Assignee: Q-CORE MEDICAL LTD., Netanya (IL)

( * ) Notice: Subject to any disclaimer, the term of this patent is extended or adjusted under 35 U.S.C. 154(b) by 0 days.

(21) Appl. No.: 15/600,740

(22) Filed: May 21, 2017

(65) Prior Publication Data

US 2017/0254482 A1    Sep. 7, 2017

Related U.S. Application Data

(63) Continuation of application No. 13/651,420, filed on Oct. 14, 2012, now Pat. No. 9,657,902, which is a
(Continued)

(30) Foreign Application Priority Data

Nov. 24, 2004  (IL) .......................... 165365
Nov. 13, 2006  (IL) .......................... 179228

(51) Int. Cl.
*F17D 3/00*    (2006.01)
*A61M 39/28*   (2006.01)
(Continued)

(52) U.S. Cl.
CPC ........... *F17D 3/00* (2013.01); *A61M 5/14228* (2013.01); *A61M 5/16813* (2013.01);
(Continued)

(58) Field of Classification Search
CPC .............. A61M 5/142; A61M 5/14228; A61M 2205/12; A61M 2205/14; F04B 43/12; F04B 43/082
See application file for complete search history.

(56) References Cited

U.S. PATENT DOCUMENTS 2,056,322 A    10/1936  Hoppe
2,393,838 A     1/1946  Tarbox
(Continued)

FOREIGN PATENT DOCUMENTS

DE    10118086 A1    7/2002
EP     0215249 A1    3/1987
(Continued)

OTHER PUBLICATIONS

Honeywell Sensing and Control, "FSSI500NSB force sensor", Golden Valley, Minnesota, USA, 1998-2004 https://www.sager.com/fss1500nsb-574989.html?utm_source=googlemerchant&utm_medium=click&utm_campaign=sager-brand&gclid=EAlaIQobChMIwIzFoKOw2w1VlbjACh0FPgPGEAQYASABEgIcofD_BwE.

*Primary Examiner* — Patrick Hamo
(74) *Attorney, Agent, or Firm* — The Roy Gross Law Firm, LLC; Roy Gross

(57) ABSTRACT

A medical device includes an interface unit body, which is configured to hold a portion of a flexible infusion tube. A hinge insert is fixed to the interface unit body and is configured to engage a hinge receptacle, which defines a hinge axis, on an infusion pump. A catch insert is fixed to the interface unit body and is configured to lock onto a catch receptacle on the infusion pump upon rotation of the mechanical interface unit about the hinge axis while the hinge insert engages the hinge receptacle, so as to bring the tube into engagement with a peristaltic mechanism of the
(Continued)

infusion pump in order to enable the peristaltic mechanism to propel a fluid through the tube.

9 Claims, 6 Drawing Sheets

Related U.S. Application Data continuation of application No. 12/464,202, filed on May 12, 2009, now Pat. No. 8,308,457, which is a continuation-in-part of application No. PCT/IL2007/001399, filed on Nov. 13, 2007, which is a continuation-in-part of application No. 11/791,599, filed as application No. PCT/IL2005/001249 on Nov. 24, 2005, now Pat. No. 8,029,253.

(51) Int. Cl.
  *A61M 5/142* (2006.01)
  *F04B 43/08* (2006.01)
  *F04B 43/12* (2006.01)
  *A61M 5/168* (2006.01)

(52) U.S. Cl.
  CPC ......... *A61M 39/281* (2013.01); *F04B 43/082* (2013.01); *F04B 43/12* (2013.01); *Y10T 137/0318* (2015.04); *Y10T 137/85978* (2015.04)

(56) References Cited

U.S. PATENT DOCUMENTS

| | | | |
|---|---|---|---|
| 2,743,898 A | 5/1956 | King |
| 2,981,115 A | 4/1961 | Beguin |
| 3,443,585 A | 5/1969 | Reinicke |
| 3,511,583 A | 5/1970 | Brown |
| 3,677,667 A | 7/1972 | Morrison |
| 3,778,195 A | 12/1973 | Bamberg |
| 3,982,722 A | 9/1976 | Bernard |
| 3,982,725 A | 9/1976 | Clark |
| 4,014,318 A | 3/1977 | Dockum et al. |
| 4,039,269 A | 8/1977 | Pickering |
| 4,155,362 A | 5/1979 | Jess |
| 4,178,138 A | 12/1979 | Iles |
| 4,236,880 A * | 12/1980 | Archibald ......... A61M 5/14224 138/30 |
| 4,270,532 A | 6/1981 | Franetzki et al. |
| 4,290,346 A | 9/1981 | Bujan |
| 4,320,781 A | 3/1982 | Bouvet et al. |
| 4,373,525 A | 2/1983 | Kobayashi |
| 4,450,375 A | 5/1984 | Siegal |
| 4,479,797 A | 10/1984 | Kobayashi et al. |
| 4,489,863 A | 12/1984 | Horchos et al. |
| 4,493,706 A | 1/1985 | Borsanyi et al. |
| 4,650,469 A | 3/1987 | Berg et al. |
| 4,671,792 A | 6/1987 | Borsanyi |
| 4,682,135 A | 7/1987 | Yamakawa |
| 4,690,673 A | 9/1987 | Bloomquist |
| 4,725,205 A | 2/1988 | Cannon et al. |
| 4,728,265 A | 3/1988 | Cannon |
| 4,741,736 A | 5/1988 | Brown |
| 4,748,003 A | 5/1988 | Riley |
| 4,755,168 A | 7/1988 | Romanelli et al. |
| 4,836,752 A | 6/1989 | Burkett |
| 4,867,744 A | 9/1989 | Borsanyi |
| 4,893,991 A | 1/1990 | Heminway et al. |
| 4,927,411 A | 5/1990 | Pastrone et al. |
| 4,954,046 A | 9/1990 | Irvin et al. |
| 4,954,256 A | 9/1990 | Degen et al. |
| 4,978,335 A | 12/1990 | Arthur, III |
| 5,074,756 A | 12/1991 | Davis |
| 5,078,683 A | 1/1992 | Sancoff et al. |
| 5,088,904 A | 2/1992 | Okada |
| 5,096,385 A | 3/1992 | Georgi et al. |
| 5,103,211 A | 4/1992 | Daoud et al. |
| 5,151,019 A | 9/1992 | Danby et al. |
| 5,152,680 A | 10/1992 | Okada |
| 5,165,874 A * | 11/1992 | Sancoff ............ A61M 5/14228 128/DIG. 12 |
| 5,213,483 A | 5/1993 | Flaherty et al. |
| 5,219,327 A | 6/1993 | Okada |
| 5,222,946 A | 6/1993 | Kamen |
| 5,246,347 A | 9/1993 | Davis |
| 5,257,978 A | 11/1993 | Haber et al. |
| 5,286,176 A | 2/1994 | Bonin |
| 5,290,158 A | 3/1994 | Okada |
| 5,308,333 A | 5/1994 | Skakoon |
| 5,338,157 A | 8/1994 | Blomquist |
| 5,395,320 A | 3/1995 | Padda et al. |
| 5,429,485 A | 7/1995 | Dodge |
| 5,485,408 A | 1/1996 | Blomquist |
| 5,499,969 A | 3/1996 | Beuchat et al. |
| 5,509,439 A | 4/1996 | Tantardini |
| 5,527,295 A | 6/1996 | Wing |
| 5,542,826 A | 8/1996 | Warner |
| 5,569,188 A | 10/1996 | Mackool |
| 5,575,309 A | 11/1996 | Connell |
| 5,575,631 A | 11/1996 | Jester |
| 5,577,891 A | 11/1996 | Loughnane et al. |
| 5,584,667 A | 12/1996 | Davis |
| 5,593,134 A | 1/1997 | Steber et al. |
| 5,601,420 A | 2/1997 | Warner et al. |
| 5,628,619 A | 5/1997 | Wilson |
| 5,658,250 A | 8/1997 | Blomquist et al. |
| 5,658,252 A | 8/1997 | Johnson |
| 5,660,529 A | 8/1997 | Hill |
| 5,669,877 A | 9/1997 | Blomquist |
| 5,683,233 A | 11/1997 | Moubayed et al. |
| 5,695,473 A | 12/1997 | Olsen |
| 5,704,584 A | 1/1998 | Winterer et al. |
| 5,742,519 A | 4/1998 | McClendon et al. |
| 5,782,805 A | 7/1998 | Meinzer et al. |
| 5,788,669 A | 8/1998 | Peterson |
| 5,791,880 A | 8/1998 | Wilson |
| 5,791,881 A | 8/1998 | Moubayed et al. |
| 5,803,712 A | 9/1998 | Davis et al. |
| 5,807,322 A | 9/1998 | Lindsey et al. |
| 5,810,323 A | 9/1998 | Winterer et al. |
| 5,853,386 A | 12/1998 | Davis et al. |
| 5,876,370 A | 3/1999 | Blomquist |
| 5,888,052 A | 3/1999 | Hill |
| 5,896,076 A | 4/1999 | van Namen |
| 5,909,724 A | 6/1999 | Nishimura et al. |
| 5,924,852 A | 7/1999 | Moubayed et al. |
| 5,935,099 A | 8/1999 | Peterson et al. |
| 5,935,106 A | 8/1999 | Olsen |
| 5,943,633 A | 8/1999 | Wilson et al. |
| 5,954,485 A | 9/1999 | Johnson et al. |
| 5,980,490 A | 11/1999 | Tsoukalis |
| 5,996,964 A | 12/1999 | Ben-Shalom |
| 6,024,539 A | 2/2000 | Blomquist |
| 6,095,189 A | 8/2000 | Ben-Shalom |
| 6,110,153 A | 8/2000 | Davis et al. |
| 6,146,109 A | 11/2000 | Davis et al. |
| 6,164,921 A | 12/2000 | Moubayed et al. |
| 6,165,874 A | 12/2000 | Powell et al. |
| RE37,074 E | 2/2001 | Danby et al. |
| 6,203,296 B1 | 3/2001 | Ray et al. |
| 6,213,723 B1 | 4/2001 | Danby et al. |
| 6,213,739 B1 | 4/2001 | Phallen et al. |
| 6,234,773 B1 | 5/2001 | Hill et al. |
| 6,241,704 B1 | 6/2001 | Peterson et al. |
| 6,261,262 B1 | 7/2001 | Briggs et al. |
| 6,280,408 B1 | 8/2001 | Sipin |
| 6,312,227 B1 | 11/2001 | Davis |
| 6,339,410 B1 | 1/2002 | Milner et al. |
| 6,347,553 B1 | 2/2002 | Morris et al. |
| 6,371,732 B1 | 4/2002 | Moubayed et al. |
| 6,422,057 B1 | 7/2002 | Anderson |
| 6,450,773 B1 | 9/2002 | Upton |
| 6,475,180 B2 | 11/2002 | Peterson et al. |
| 6,519,569 B1 | 2/2003 | White et al. |
| 6,537,244 B2 | 3/2003 | Paukovits et al. |

(56) References Cited

U.S. PATENT DOCUMENTS

| | | |
|---|---|---|
| 6,544,171 B2 | 4/2003 | Beetz et al. |
| 6,558,347 B1 | 5/2003 | Jhuboo et al. |
| 6,572,604 B1 | 6/2003 | Platt et al. |
| 6,622,542 B2 | 9/2003 | Derek et al. |
| 6,648,861 B2 | 11/2003 | Platt et al. |
| 6,692,241 B2* | 2/2004 | Watanabe ......... A61M 5/14228 417/477.2 |
| 6,733,476 B2 | 5/2004 | Christenson et al. |
| 6,742,992 B2 | 6/2004 | Davis |
| 6,749,587 B2 | 6/2004 | Flaherty |
| 6,768,425 B2 | 7/2004 | Flaherty et al. |
| 6,788,199 B2 | 9/2004 | Crabtree et al. |
| 6,790,198 B1 | 9/2004 | White et al. |
| 6,902,549 B2 | 6/2005 | Marmaropoulos et al. |
| 6,942,473 B2* | 9/2005 | Abrahamson ..... A61M 5/14228 417/474 |
| 7,018,361 B2 | 3/2006 | Gillespie, Jr. et al. |
| 7,022,075 B2 | 4/2006 | Grunwald et al. |
| 7,048,720 B1 | 5/2006 | Thorne, Jr. et al. |
| 7,059,840 B2 | 6/2006 | Corwin et al. |
| 7,122,026 B2 | 10/2006 | Rogers et al. |
| 7,131,966 B1 | 11/2006 | Tamari |
| 7,163,385 B2 | 1/2007 | Gharib et al. |
| 7,347,836 B2 | 3/2008 | Peterson et al. |
| 7,525,432 B2 | 4/2009 | Jackson |
| 7,556,481 B2 | 7/2009 | Moubayed |
| 7,645,258 B2 | 1/2010 | White et al. |
| 7,654,976 B2 | 2/2010 | Peterson et al. |
| 7,695,255 B2 | 4/2010 | Ben-Shalom et al. |
| 7,698,156 B2 | 4/2010 | Martucci et al. |
| 7,704,227 B2 | 4/2010 | Moberg et al. |
| 7,762,795 B2 | 7/2010 | Moubayed |
| 7,840,260 B2 | 11/2010 | Epley |
| 7,892,332 B2 | 2/2011 | Prisco et al. |
| 7,896,834 B2 | 3/2011 | Smisson, III et al. |
| 7,935,102 B2 | 5/2011 | Breznock et al. |
| 7,938,796 B2 | 5/2011 | Moubayed et al. |
| 7,963,946 B2 | 6/2011 | Moubayed et al. |
| 7,998,121 B2 | 8/2011 | Stringham |
| 8,025,634 B1 | 9/2011 | Moubayed et al. |
| 8,029,253 B2 | 10/2011 | Rotem et al. |
| 8,142,400 B2 | 3/2012 | Rotem et al. |
| 8,182,445 B2 | 5/2012 | Moubayed et al. |
| 8,197,235 B2 | 6/2012 | Davis |
| 8,214,231 B2 | 7/2012 | Martucci et al. |
| 8,234,128 B2 | 7/2012 | Martucci et al. |
| 8,241,018 B2 | 8/2012 | Harr |
| 8,257,654 B2 | 9/2012 | Maus et al. |
| 8,308,457 B2 | 11/2012 | Rotem et al. |
| 8,334,768 B2 | 12/2012 | Eaton et al. |
| 8,337,168 B2 | 12/2012 | Rotem et al. |
| 8,343,111 B2 | 1/2013 | Beck et al. |
| 8,352,290 B2 | 1/2013 | Bartz et al. |
| 8,363,583 B2 | 1/2013 | Jia et al. |
| 8,371,832 B2 | 2/2013 | Rotem et al. |
| 8,444,587 B2 | 5/2013 | Kelly et al. |
| 8,489,427 B2 | 7/2013 | Simpson et al. |
| 8,535,025 B2 | 9/2013 | Rotem et al. |
| 8,579,816 B2 | 11/2013 | Kamath et al. |
| 8,666,367 B2 | 3/2014 | Sharp et al. |
| 8,672,875 B2 | 3/2014 | Vanderveen et al. |
| 8,678,793 B2 | 3/2014 | Goldor et al. |
| 8,920,144 B2 | 12/2014 | Rotem et al. |
| 9,056,160 B2 | 6/2015 | Rotem et al. |
| 2001/0029321 A1 | 10/2001 | Beetz et al. |
| 2002/0056675 A1 | 5/2002 | Hegde |
| 2002/0094287 A1 | 7/2002 | Davis |
| 2002/0156402 A1 | 10/2002 | Woog et al. |
| 2002/0165503 A1 | 11/2002 | Morris et al. |
| 2003/0034887 A1 | 2/2003 | Crabtree et al. |
| 2003/0040700 A1 | 2/2003 | Hickle et al. |
| 2003/0065536 A1 | 4/2003 | Hansen et al. |
| 2003/0109988 A1 | 6/2003 | Geissler et al. |
| 2003/0140928 A1 | 7/2003 | Bui et al. |
| 2003/0141981 A1 | 7/2003 | Bui et al. |
| 2003/0182586 A1 | 9/2003 | Numano |
| 2004/0167804 A1 | 8/2004 | Simpson et al. |
| 2004/0172222 A1 | 9/2004 | Simpson et al. |
| 2004/0181314 A1 | 9/2004 | Zaleski |
| 2004/0191112 A1 | 9/2004 | Hill et al. |
| 2004/0204673 A1 | 10/2004 | Flaherty |
| 2004/0204685 A1 | 10/2004 | Wright et al. |
| 2004/0235446 A1 | 11/2004 | Flaherty et al. |
| 2005/0001369 A1 | 1/2005 | Cross |
| 2005/0022274 A1 | 1/2005 | Campbell et al. |
| 2005/0055242 A1 | 3/2005 | Bello et al. |
| 2005/0088409 A1 | 4/2005 | Van Berkel |
| 2005/0112001 A1 | 5/2005 | Bahnen et al. |
| 2005/0171501 A1 | 8/2005 | Kelly |
| 2005/0191196 A1 | 9/2005 | Tanner et al. |
| 2005/0214146 A1 | 9/2005 | Corwin et al. |
| 2006/0051218 A1 | 3/2006 | Harttig |
| 2006/0083644 A1 | 4/2006 | Zumbrum et al. |
| 2006/0173419 A1 | 8/2006 | Malcolm |
| 2006/0213249 A1 | 9/2006 | Uram et al. |
| 2007/0032098 A1 | 2/2007 | Bowles et al. |
| 2007/0048161 A1 | 3/2007 | Moubayed |
| 2007/0060872 A1 | 3/2007 | Hall et al. |
| 2007/0118405 A1 | 5/2007 | Campbell et al. |
| 2007/0135866 A1 | 6/2007 | Baker et al. |
| 2007/0154336 A1 | 7/2007 | Miyazaki et al. |
| 2007/0217931 A1 | 9/2007 | Estes et al. |
| 2007/0269324 A1 | 11/2007 | Goldor et al. |
| 2008/0015506 A1 | 1/2008 | Davis |
| 2008/0065007 A1 | 3/2008 | Peterson et al. |
| 2008/0065016 A1 | 3/2008 | Peterson et al. |
| 2008/0067462 A1 | 3/2008 | Miller et al. |
| 2008/0071251 A1 | 3/2008 | Moubayed et al. |
| 2008/0095649 A1 | 4/2008 | Ben-Shalom et al. |
| 2008/0144560 A1 | 6/2008 | Jia et al. |
| 2008/0145249 A1 | 6/2008 | Smisson et al. |
| 2008/0146995 A1 | 6/2008 | Smisson et al. |
| 2008/0275307 A1 | 11/2008 | Poschmann |
| 2009/0088675 A1 | 4/2009 | Kelly et al. |
| 2009/0163864 A1 | 6/2009 | Breznock et al. |
| 2009/0203329 A1 | 8/2009 | White et al. |
| 2009/0221964 A1* | 9/2009 | Rotem ............... A61M 5/14228 604/151 |
| 2009/0240201 A1 | 9/2009 | Rotem et al. |
| 2009/0270810 A1 | 10/2009 | DeBelser et al. |
| 2009/0300507 A1 | 12/2009 | Raghavan et al. |
| 2009/0317268 A1 | 12/2009 | Rotem et al. |
| 2010/0016781 A1 | 1/2010 | Nakayama et al. |
| 2010/0036322 A1* | 2/2010 | Rotem ............... A61M 5/14228 604/151 |
| 2010/0082001 A1 | 4/2010 | Beck et al. |
| 2010/0168545 A1 | 7/2010 | Kamath et al. |
| 2010/0211002 A1 | 8/2010 | Davis |
| 2010/0228223 A1 | 9/2010 | Williams et al. |
| 2010/0234708 A1 | 9/2010 | Buck et al. |
| 2010/0279652 A1 | 11/2010 | Sharp et al. |
| 2011/0148624 A1 | 6/2011 | Eaton et al. |
| 2011/0152772 A1 | 6/2011 | Rotem et al. |
| 2011/0152831 A1 | 6/2011 | Rotem et al. |
| 2011/0167133 A1 | 7/2011 | Jain |
| 2011/0251856 A1 | 10/2011 | Maus et al. |
| 2011/0264043 A1 | 10/2011 | Kotnik et al. |
| 2011/0276000 A1* | 11/2011 | Stringham ............ A61M 5/142 604/151 |
| 2011/0282291 A1 | 11/2011 | Ciccone |
| 2011/0318208 A1 | 12/2011 | Goldor et al. |
| 2012/0059389 A1 | 3/2012 | Larson et al. |
| 2012/0062387 A1 | 3/2012 | Vik et al. |
| 2012/0136305 A1 | 5/2012 | Gagliardoni et al. |
| 2012/0241525 A1 | 9/2012 | Borges et al. |
| 2013/0006666 A1 | 1/2013 | Schneider et al. |
| 2013/0046508 A1 | 2/2013 | Sur et al. |
| 2013/0116620 A1 | 5/2013 | Rotem et al. |
| 2013/0116623 A1 | 5/2013 | Rotem et al. |
| 2013/0142670 A1 | 6/2013 | Rotem et al. |
| 2013/0209275 A1 | 8/2013 | Rotem et al. |
| 2013/0279370 A1 | 10/2013 | Eitan et al. |
| 2013/0345623 A1 | 12/2013 | Kopperschmidt et al. |
| 2014/0005631 A1 | 1/2014 | Rotem et al. |

(56) References Cited

U.S. PATENT DOCUMENTS

| | | |
|---|---|---|
| 2014/0119954 A1 | 5/2014 | Schweitzer et al. |
| 2014/0197824 A1 | 7/2014 | Gillespie et al. |
| 2014/0222377 A1 | 8/2014 | Bitan et al. |
| 2014/0276564 A1 | 9/2014 | Schneider |
| 2014/0369872 A1 | 12/2014 | Goldor et al. |
| 2014/0378901 A1 | 12/2014 | Rotem et al. |
| 2015/0038187 A1 | 2/2015 | Ho et al. |
| 2015/0073338 A1 | 3/2015 | Waldhoff et al. |
| 2015/0105726 A1 | 4/2015 | Qi et al. |
| 2015/0137988 A1 | 5/2015 | Gravenstein et al. |
| 2015/0141955 A1 | 5/2015 | Ruchti et al. |
| 2015/0172921 A1 | 6/2015 | Wang et al. |
| 2015/0182694 A1 | 7/2015 | Rosinko |
| 2015/0192120 A1 | 7/2015 | Rotem et al. |

FOREIGN PATENT DOCUMENTS

| | | | |
|---|---|---|---|
| EP | 0225158 A2 | 6/1987 | |
| EP | 0315312 A1 | 5/1989 | |
| EP | 0429866 A1 | 6/1991 | |
| EP | 0483794 A1 | 5/1992 | |
| EP | 0858812 A2 | 8/1998 | |
| EP | 1031358 A1 | 8/2000 | |
| EP | 1350955 A2 | 10/2003 | |
| EP | 1557186 A1 | 7/2005 | |
| EP | 1611834 A2 | 1/2006 | |
| EP | 1485149 B1 | 7/2008 | |
| FR | 2632529 A1 | 12/1989 | |
| FR | 2753236 A1 | 3/1998 | |
| JP | S6043188 A | 3/1985 | |
| JP | H06169992 A | 6/1994 | |
| JP | 2002057738 A | 2/2002 | |
| JP | 2004141418 A | 5/2004 | |
| WO | 8400691 A1 | 3/1984 | |
| WO | 9116933 A1 | 11/1991 | |
| WO | 9325816 A1 | 12/1993 | |
| WO | 9408647 A1 | 4/1994 | |
| WO | 9603168 A1 | 2/1996 | |
| WO | 9630679 A1 | 10/1996 | |
| WO | 9734084 A1 | 9/1997 | |
| WO | 9804301 A1 | 2/1998 | |
| WO | 9813080 A2 | 4/1998 | |
| WO | 9847551 A1 | 10/1998 | |
| WO | 99/58178 A1 | 11/1999 | |
| WO | 0139816 A2 | 6/2001 | |
| WO | 0165232 A1 | 9/2001 | |
| WO | 0236044 A2 | 5/2002 | |
| WO | 0238204 A2 | 5/2002 | |
| WO | 0249509 A2 | 6/2002 | |
| WO | 2002068015 A2 | 9/2002 | |
| WO | 03027503 A1 | 4/2003 | |
| WO | 03080158 A1 | 10/2003 | |
| WO | 2004070548 A2 | 8/2004 | |
| WO | 2004093648 A2 | 11/2004 | |
| WO | 2005089263 A2 | 9/2005 | |
| WO | 2006/056986 A1 | 6/2006 | |
| WO | 2007133259 A1 | 11/2007 | |
| WO | 2008036658 A2 | 3/2008 | |
| WO | 2008059492 A2 | 5/2008 | |
| WO | 2008059493 A2 | 5/2008 | |
| WO | 2008059494 A2 | 5/2008 | |
| WO | 2008059495 A2 | 5/2008 | |
| WO | 2008059496 A2 | 5/2008 | |
| WO | 2008059498 A2 | 5/2008 | |
| WO | 2008059499 A2 | 5/2008 | |
| WO | 2008130644 A1 | 10/2008 | |
| WO | 2010053702 A1 | 5/2010 | |
| WO | 2010053703 A1 | 5/2010 | |
| WO | 2010091313 A2 | 8/2010 | |
| WO | 2011128850 A2 | 10/2011 | |
| WO | 2012095827 A1 | 7/2012 | |
| WO | 2012095829 A2 | 7/2012 | |
| WO | 2013001425 A2 | 1/2013 | |
| WO | 2013/028704 A1 | 2/2013 | |
| WO | 2013/090748 A1 | 6/2013 | |

* cited by examiner

PERISTALTIC INFUSION PUMP WITH LOCKING MECHANISM

CROSS-REFERENCE TO RELATED APPLICATIONS

This application is a continuation-in-part of U.S. patent application Ser. No. 11/791,599, filed May 24, 2007, in the national please of PCT/IL2005/001249, filed Nov. 24, 2005, and of PCT Patent Application PCT/IL2007/001399, filed Nov. 13, 2007. The disclosures of all of these related applications are incorporated herein by reference.

FIELD OF THE INVENTION

The present invention relates generally to medical devices, and specifically to infusion pumps.

BACKGROUND OF THE INVENTION

Various types of medical infusion pumps are known in the art. One common type of infusion pump is a peristaltic pump, in which fluid is made to flow through an elastic tube by external compression of the tube. Typically, a peristaltic mechanism, such as a set of cams or fingers, compresses the tube in a cyclic pattern at a sequence of locations along the length of the tube, so as to cause the fluid to flow through the tube at a desired volumetric rate. Peristaltic infusion pumps are described, for example, in U.S. Pat. Nos. 5,290,158, 5,395,320, and 5,807,322, whose disclosures are incorporated herein by reference, as well as in the above-mentioned PCT patent applications.

SUMMARY OF THE INVENTION

One advantage of peristaltic pumps in medical applications is that the pump mechanism is external to the flexible tube containing the fluid, thus preserving the sterility of the fluid flowing through the tube. The tube is typically part of a disposable infusion kit, while the pump itself (which may include the complete pumping mechanism, as well as a pressure sensor module) is reused many times. Embodiments of the present invention that are described hereinbelow provide devices and methods that simplify the task of attaching the infusion tube to the pump prior to use, while ensuring a secure, reliable mechanical connection between the pump mechanism and the tube.

There is therefore provided, in accordance with an embodiment of the present invention, a medical apparatus, including an infusion pump, which includes a pump body and a peristaltic mechanism, which protrudes from the pump body and is configured to exert a force on a flexible infusion tube so as to propel a fluid through the tube. A hinge receptacle is fixed to the pump body and defines a hinge axis, and a catch receptacle is also fixed to the pump body. A mechanical interface unit is configured to hold a portion of the tube, and includes a hinge insert, which is configured to engage the hinge receptacle. A catch insert is configured to lock onto the catch receptacle upon rotation of the mechanical interface unit about the hinge axis while the hinge insert engages the hinge receptacle, so as to bring the tube into engagement with the peristaltic mechanism.

In a disclosed embodiment, the peristaltic mechanism includes multiple fingers, which are driven to compress and release the tube in a predetermined cyclic pattern.

In some embodiments, the peristaltic mechanism has a linear configuration, and the mechanical interface has an elongated shape corresponding to the linear configuration of the peristaltic mechanism.

In one embodiment, the hinge receptacle includes an axle, and the hinge insert includes a saddle, which fits over the axle. The axle and saddle may be split so as to define a channel for receiving the portion of the tube. Additionally or alternatively, the catch insert includes a tooth, and the catch receptacle includes an elastic catch.

In some embodiments, the pump body includes a rim surrounding the peristaltic mechanism, and the mechanical interface unit includes collars, which are fixed to opposing ends of the portion of the tube and lodge against the rim. The infusion pump may include a door, which closes over the rim so as to enclose the peristaltic mechanism. The rim may have openings shaped to receive the tube so that the tube extends through the openings when the door is closed. Typically, the collars are configured to lodge inside the rim and have respective diameters that are larger than the openings so as to prevent axial motion of the tube after the door has been closed.

In a disclosed embodiment, the mechanical interface unit includes an anti-free-flow mechanism, which is configured to prevent flow of the fluid through the portion of the tube until the tube has been brought into the engagement with the peristaltic mechanism. Typically, the anti-free-flow mechanism can be opened manually prior to the engagement of the tube with the peristaltic mechanism, and the infusion pump includes a key, which is fixed to the pump body and is configured to release the anti-free-flow mechanism so as to prevent the flow of the fluid through the portion of the tube when mechanical interface unit is disengaged from the pump.

There is also provided, in accordance with an embodiment of the present invention, a medical device, including an interface unit body, which is configured to hold a portion of a flexible infusion tube. A hinge insert is fixed to the interface unit body and is configured to engage a hinge receptacle, which defines a hinge axis, on an infusion pump. A catch insert is fixed to the interface unit body and is configured to lock onto a catch receptacle on the infusion pump upon rotation of the mechanical interface unit about the hinge axis while the hinge insert engages the hinge receptacle, so as to bring the tube into engagement with a peristaltic mechanism of the infusion pump in order to enable the peristaltic mechanism to propel a fluid through the tube.

In a disclosed embodiment, the device includes collars, which are fixed to opposing ends of the portion of the tube and are configured to lodge against a rim surrounding the peristaltic mechanism on the infusion pump. The collars may include connectors, which connect the portion of the flexible infusion tube in the housing to upstream and downstream tube segments.

There is additionally provided, in accordance with an embodiment of the present invention, a method for infusion, including providing a mechanical interface unit, which holds a portion of a flexible infusion tube and includes a hinge insert and a catch insert. The hinge insert in inserted into a hinge receptacle, which defines a hinge axis, on an infusion pump. The mechanical interface unit is rotated about the hinge axis while the hinge insert engages the hinge receptacle, so as to bring the tube into engagement with a peristaltic mechanism of the infusion pump. The infusion pump is actuated while the tube is in engagement with the peristaltic mechanism so as to propel a fluid through the tube.

The present invention will be more fully understood from the following detailed description of the embodiments thereof, taken together with the drawings in which:

DETAILED DESCRIPTION OF EMBODIMENTS

Figure 1:
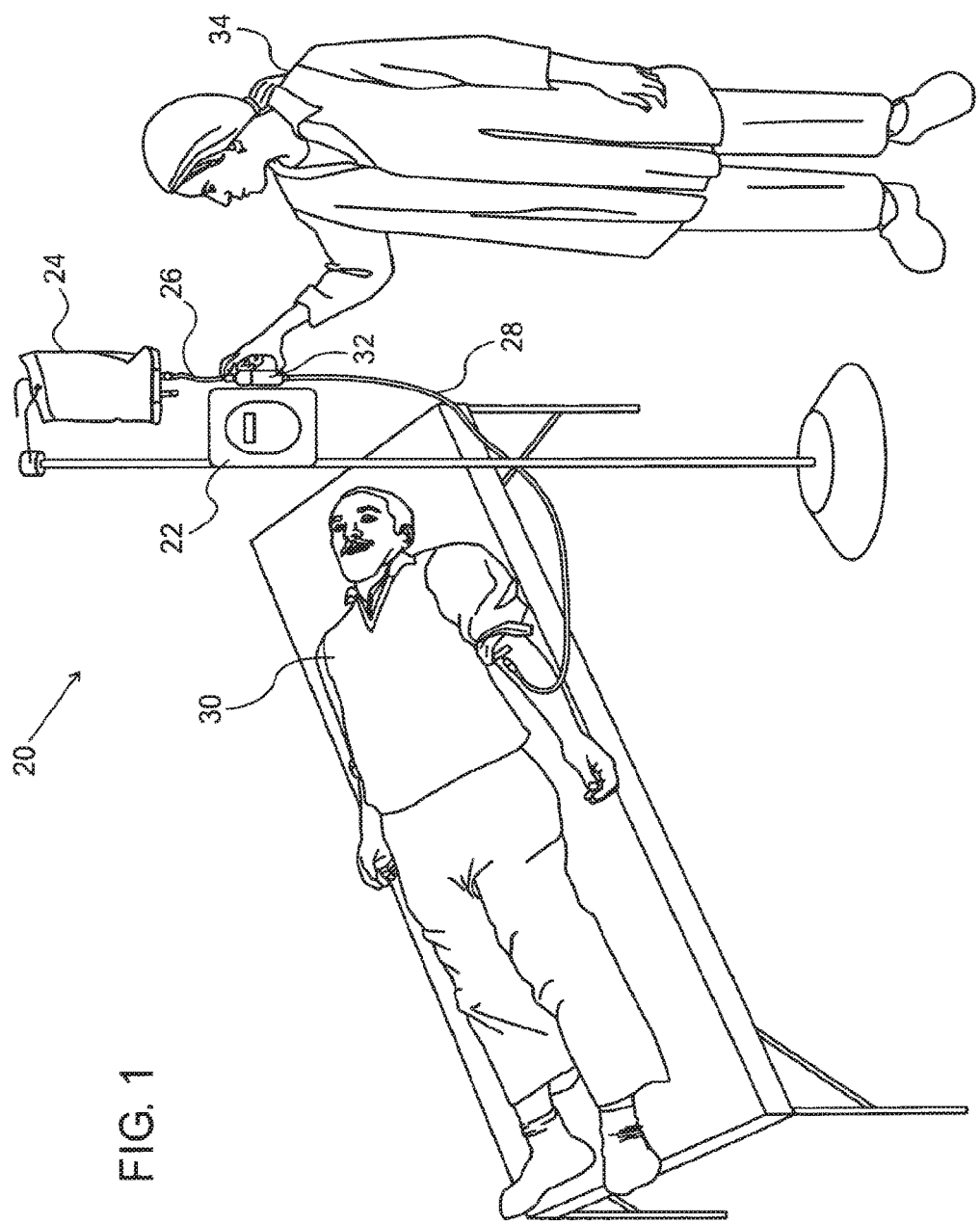
FIG. 1 is a schematic, pictorial illustration of a medical infusion system, in accordance with an embodiment of the present invention.

FIG. 1 is a schematic, pictorial illustration of a medical infusion system 20, in accordance with an embodiment of the present invention. System 20 comprises a peristaltic infusion pump 22, which pumps an infusion fluid from a reservoir 24, through an upstream tube segment 26 (commonly referred to as the "supply line") and a downstream tube segment 28 (commonly referred to as the "patient line"), into a vein of a patient 30. This particular type of infusion system is shown here by way of illustration, but the principles of the present invention, as described hereinbelow, may likewise be applied to other types of peristaltic pumps and in substantially any sort of application that uses such pumps, such as delivery of drugs and of both enteral and parenteral nutrition. Although the pictured embodiment represents a clinical environment, the devices and methods described herein are also suitable for ambulatory and home use, particularly since they can operate even when the pump and reservoir are at the same level as or lower than the patient.

Tube segments 26 and 28 are connected to a mechanical interface unit 32, which couples to pump 32 in a manner that is shown and explained below in greater detail. Unit 32 contains a tube portion (not shown in FIG. 1) that is connected in series with tube segments 26 and 28, thus defining a flow path from reservoir 24 to patient 30. In a typical implementation, tube segments 26 and 28 comprise polyvinyl chloride (PVC), while the portion of the tube in unit 32 comprises silicone rubber. Tube segments 26 and 28 and the portion of the tube in unit 32 may thus be regarded as a single tube. Alternatively, the tube segments and the portion of the tube in unit 32 may be fabricated as a unitary element from silicone or from another material with similar properties. The term "tube," in the context of the present patent application and in the claims, should thus be understood as referring both to unitary tubes and to any arrangement of tube segments and portions in series that defines a tube-like flow path.

As shown in detail in the figures that follow, mechanical interface unit 32 couples with pump 22 so as to bring the tube into engagement with the peristaltic mechanism of the pump. Typically, unit 32 is supplied as a pre-assembled, disposable kit, along with tube segments 26 and 28. Unit 32 is constructed so as to enable an operator 34 to connect the unit to pump 22 stably and reliably by fitting the unit against the pump and snapping it into place with only light pressure. Because the connection between unit 32 and pump 22 is self-aligning, operators are able to perform this operation with a single hand, after only minimal training. After use, unit 32 may be snapped off pump 22 and discarded together with the tube.

Figure 2:
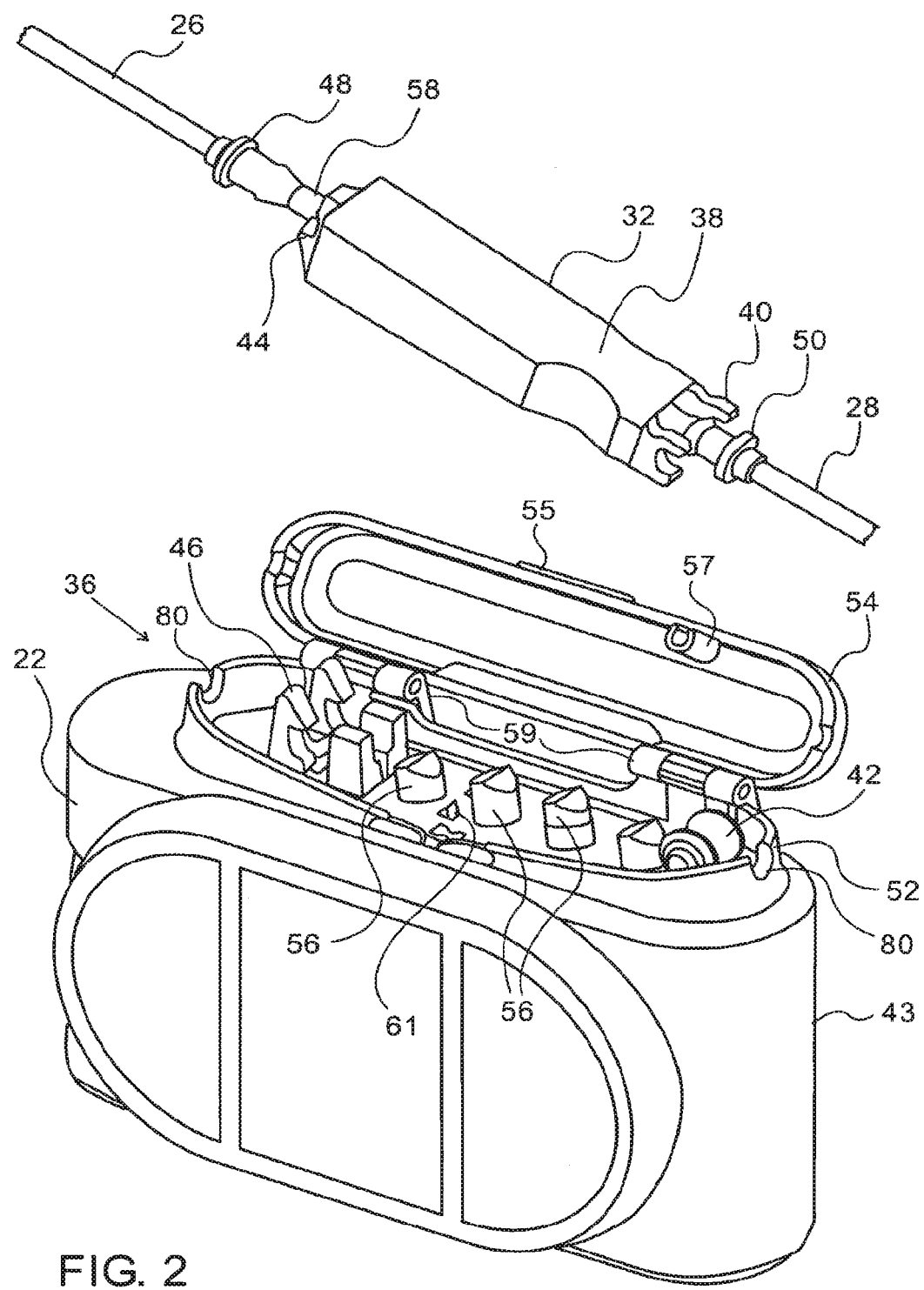
FIG. 2 is a schematic, pictorial illustration showing coupling of a mechanical interface unit with an infusion tube to an infusion pump, in accordance with an embodiment of the present invention.
Figure 3:
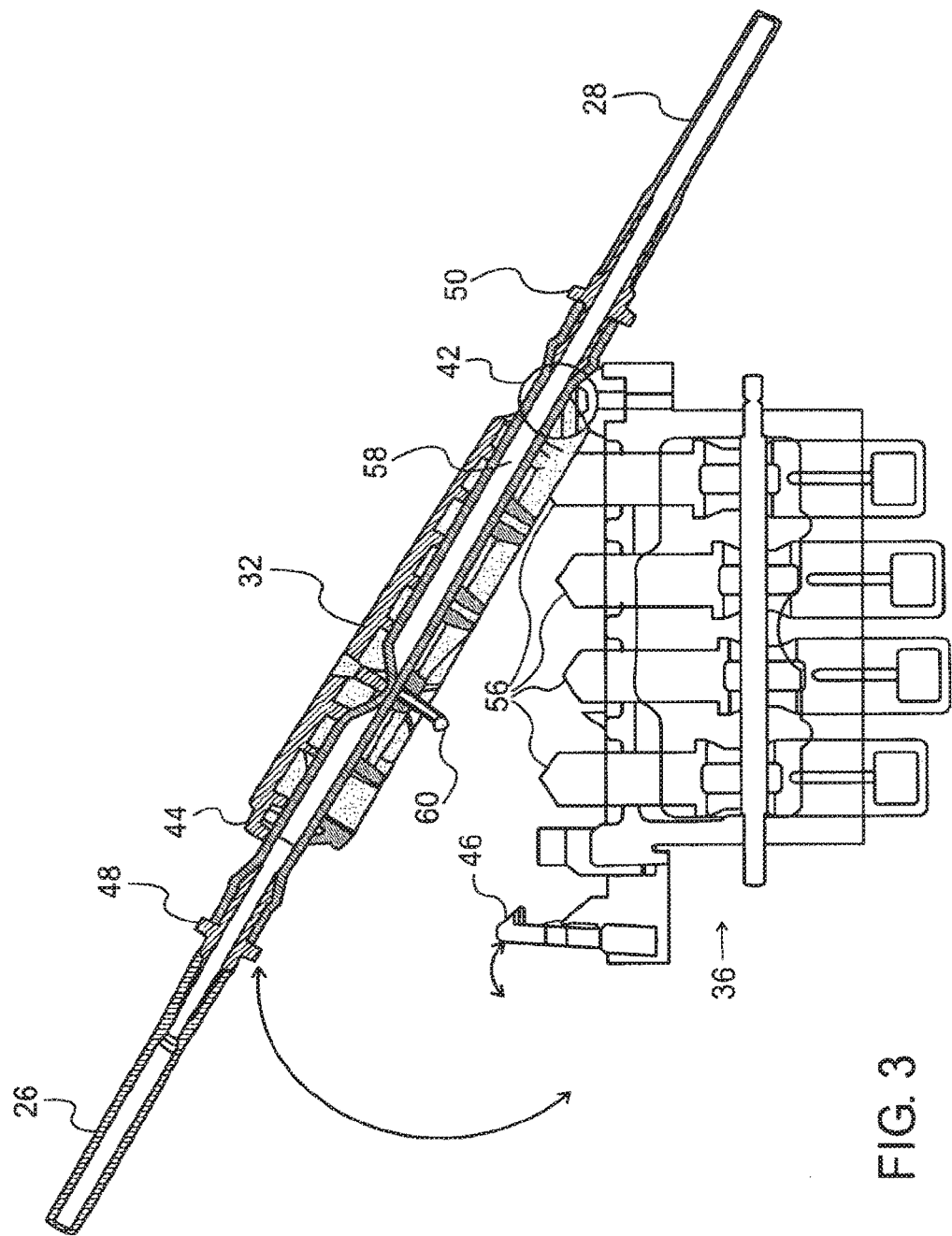
FIG. 3 is a schematic, sectional illustration of a part of an infusion pump and a mechanical interface unit during coupling of the mechanical interface unit to the infusion pump, in accordance with an embodiment of the present invention.

Reference is now made to FIGS. 2 and 3, which schematically show details of pump 22 and of mechanical interface unit 32 during preliminary stages of attaching the unit to the pump, in accordance with an embodiment of the present invention. FIG. 2 is a pictorial view, while FIG. 3 shows details of the mechanical interface unit and of a peristaltic mechanism 36 of the pump in sectional view.

Mechanical interface unit 32 comprises a body 38, which hold a portion 58 of the flexible infusion tube. In the embodiment shown in the figures, portion 58 of the tube is connected to segments 26 and 28 by connectors 48 and 50, respectively. Body 38 has an elongated shape, corresponding to the linear configuration of mechanism 36. Mechanism 36 comprises multiple fingers 56, which move up and down to compress and release tube portion 58 in a predetermined cyclic pattern, so as to propel fluid downstream from tube segment 26 to tube segment 28. Details of the operation of this sort of multi-finger peristaltic mechanism are described in the above-mentioned U.S. patent application Ser. No. 11/791,599 and in PCT Patent Applications PCT/IL2007/001398 and PCT/IL2007/001400, filed Nov. 13, 2007, whose disclosures are incorporated herein by reference.

Unit 32 comprises a hinge insert 40 at one end of body 38 (in this case, the downstream end) and a catch insert 44 at the other (upstream) end. To assemble unit onto pump 22, the operator first brings hinge insert into engagement with a hinge receptacle 42 on a body 43 of the pump. In this position, unit 32 is aligned in a plane of peristaltic mechanism 36 (i.e., the plane of the page in FIG. 3), but is able to rotate within the plane about an axis defined by the hinge receptacle. The operator rotates unit 32 about this axis, while the hinge insert engages the hinge receptacle, until catch insert engages and locks onto a catch receptacle 46 on the pump body. The catch receptacle is spring-loaded (or otherwise elastic) so that it slides over and then locks onto the catch insert as the operator presses unit 32 down against pump 22. Once engaged and locked in this manner, movement of unit 32 is restricted in all directions. Unit 32 may subsequently be released from pump 22 simply by opening the catch and rotating the unit away from the pump.

The rotational mode of assembly described above is advantageous in that it ensures accurate alignment of tube portion 58 with mechanism 36, even in one-handed operation. Consequently, good flow accuracy is achieved without the need for very careful insertion of the tube into the pump. The inventors have found that the combination of this sort of mechanical interface unit with the type of peristaltic pump described in the above-mentioned patent applications gives better than 2.5% accuracy in flow control over long periods of time.

The position of hinge receptacle 42 may be pre-adjusted so that interface unit 32, when engaged and locked onto pump 22, is properly located relative to fingers 56. For example, the hinge receptacle may be connected to pump body 43 by a single screw (not shown), which permits the receptacle to be moved and then tightened in place in a factory calibration procedure. Because the hinge receptacle is located on the downstream side of mechanism 36, this sort of calibration can be used to find the optimal balance between pressure buildup and energy consumption for propelling fluid at high pressure.

Furthermore, this mode of assembly gives the operator a mechanical advantage in closing the catch insert against the catch receptacle, so that relatively little force is needed to make a secure connection. In a clinical version of system 20, the inventor has found that less than 2 kg of force, typically about 1.2 kg, is sufficient for this purpose.

Another advantage of mechanical interface unit 32 and the mating structure on pump 22 is that they ensure that the tube will be assembled onto the pump in the proper direction: Because one type of mating connector is used at the upstream end of unit 32, and a different type of mating connector is used at the downstream end, it is impossible for the operator to accidentally attach the tube in the reverse direction.

In the embodiment pictured in the figures, hinge receptacle 42 has the form of a split axle, while hinge insert 40 has the form of a split saddle. At the other end of unit 32, catch insert 44 has the form of a split tooth, while catch receptacle 46 comprises a dual, concave catch. Tube portion 58 thus passes through the opening between the sides of insert 40, receptacle 42, insert 44 and receptacle 46. This particular configuration of the hinge and catch parts of pump 22 and unit 32 has been found to provide mechanical stability, durability and ease of assembly.

On the other hand, other configurations of the hinge and catch parts are also possible, as will be apparent to those skilled in the art, and are considered to be within the scope of the present invention. For example, the "male" and "female" elements on the interface unit and pump body may be reversed, so that the hinge and catch inserts on the interface unit have the form of an axle and elastic catch, while the hinge and catch receptacles on the pump have the form of a saddle and tooth. Other suitable hinge and catch arrangements are described in the above-mentioned U.S. patent application Ser. No. 11/791,599.

After assembly of interface unit 32 onto pump 22, a cover 54 may be closed against a rim 52 over the unit for added security. A locking mechanism 55 on the cover prevents accidental opening. Pump 22 may comprise a sensor (not shown) for detecting whether cover 54 is closed, such as a magnetic sensor, which detects the proximity of a magnet 57 attached to the cover. Until the operator is ready to close the cover, however, spring-loaded hinges 59 hold the cover open so that it does not interfere with handling of the interface unit.

Interface unit 32 also comprises an anti-free-flow mechanism 60, which closes off tube portion 58 until the interface unit has been securely connected to pump 22, in order to prevent uncontrolled flow of infusion fluid into the patient's body. Mechanism 60 may be opened manually if necessary, and opens automatically when the interface unit is mounted on the pump. A key 61 on the pump body (FIG. 2) releases mechanism 60 if the mechanism was opened manually before mounting interface unit 32 on the pump, so as to ensure that the mechanism closes (and prevents inadvertent free flow) when the interface unit is disengaged from the pump. Details of this sort of anti-free-flow mechanism mechanism are described in the above-mentioned U.S. patent application Ser. No. 11/791,599 and in PCT Patent Application PCT/IL2007/001405, filed Nov. 13, 2007, whose disclosure is incorporated herein by reference.

Figure 4:
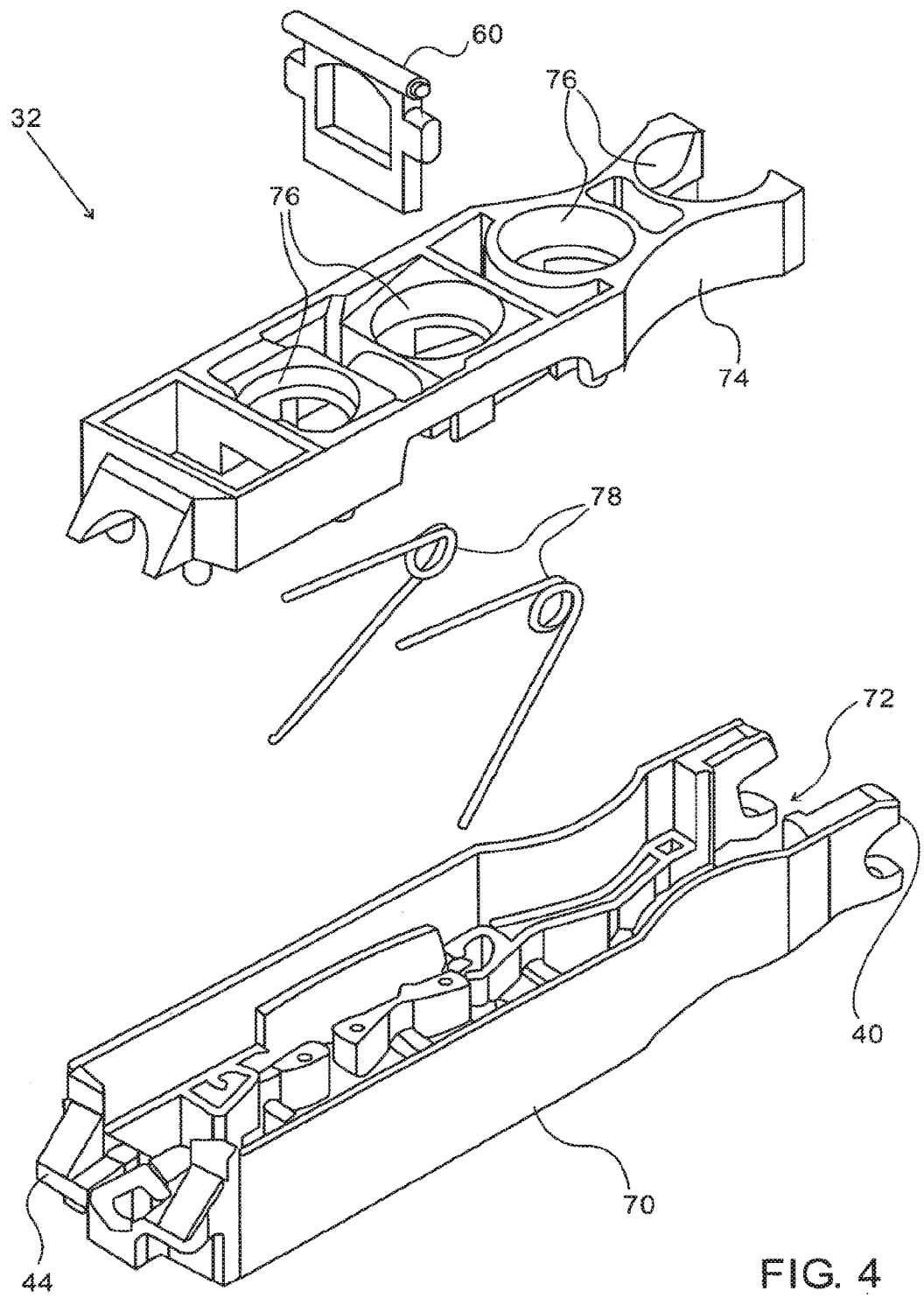
FIG. 4 is a schematic, exploded view of a mechanical interface unit, in accordance with an embodiment of the present invention.

FIG. 4 is a schematic, exploded view of interface unit 32, in accordance with an embodiment of the present invention. Unit 32 comprises an outer shell 70 and an inner shell 74, which define a central channel 72 for receiving tube portion 58. To assemble unit 32, tube portion 58 is placed in channel 72, and shells 70 and 74 are then fitted together, thus holding the tube portion securely in place. Anti-free-flow mechanism 60 is mounted in a slot in unit 32 against springs 78, which hold the mechanism in its closed position. (Alternatively, a single spring may be used for this purpose.) Shell 74 contains finger holes 76, through which fingers 56 protrude in order to engage and compress the tube portion inside.

Figure 5:
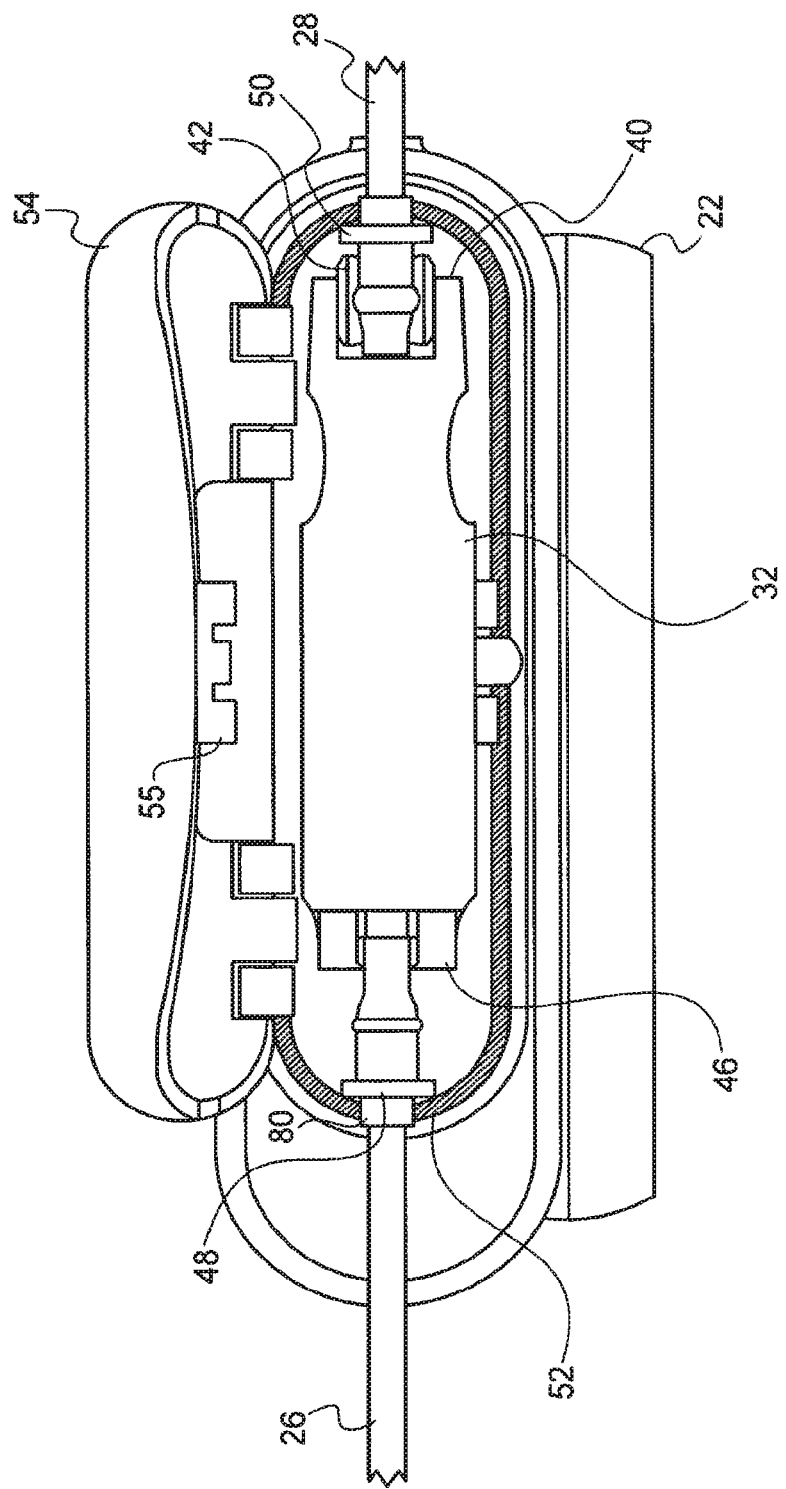
FIG. 5 is a schematic side view of an infusion pump to which a mechanical interface unit with an infusion tube has been coupled, in accordance with an embodiment of the present invention.
Figure 6:
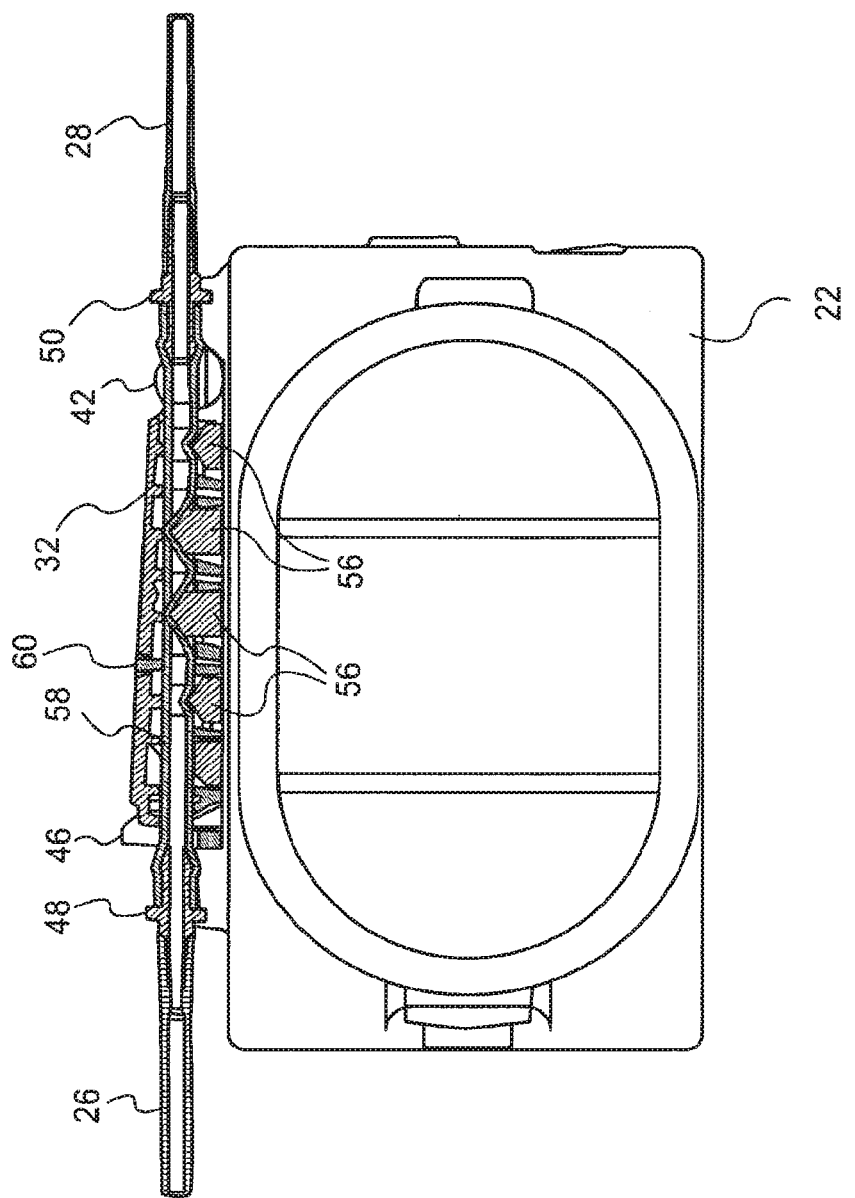
FIG. 6 is a schematic, frontal, partially sectional view of an infusion pump to which a mechanical interface unit with an infusion tube has been coupled, in accordance with an embodiment of the present invention.

Reference is now made to FIGS. 5 and 6, which show interface unit 32 assembled onto pump 22, in accordance with an embodiment of the present invention. FIG. 5 is a side view, while FIG. 6 is a frontal, partly sectional view. In these figures, catch receptacle 46 has closed over catch insert 44, thus bringing tube portion 58 into engagement with peristaltic mechanism 36 of pump 22. The peristaltic mechanism is thus able to propel the infusion fluid through the tube. Tube segments 26 and 28 protrude through holes 80 in rim 52, which are similar in shape and diameter to the tube segments. Collars on connectors 48 and 50, which have a larger diameter than the holes, lodge against the inner side of rim 52, thus enhancing the stability and security of unit 32, particularly against pulling forces that may be exerted on tubes 26 and 28. Anti-free-flow mechanism 60 is held open. Fingers 56 alternately compress and release tube portion in the appropriate pattern, at a frequency chosen to give the desired volumetric flow of fluid through the tube.

Although the embodiment shown in the figures uses a particular type of linear finger-based mechanism, the principles of the present invention may similarly be applied to peristaltic pumps using other types of mechanisms, including cam-based mechanisms, as well as circular mechanisms. It will thus be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. An infusion system comprising:
   a removable mechanical interface unit to support in a fixed position a tube through which a fluid flows;
   a device body comprising a hinge receptacle defining a hinge axis; a catch receptacle configured to receive said mechanical interface unit through which the tube passes; and a peristaltic pump connected to said body and positioned to propel fluid through the tube when the mechanical interface unit is engaged within said receptacle;
   wherein said mechanical interface unit comprises:
      an anti-free flow mechanism biased towards a safety default closed state to prevent flow of fluid through the tube when said interface unit is disengaged from said receptacle, and which anti-free flow mechanism is mechanically forced into an opened state by: (a) a key structure functionally associated with said receptacle and which applies a force on said anti-free flow mechanism when said interface unit is engaged, and (b) a manual override structure functionally associated with said anti-free flow mechanism is reconfigured it into a default open state;

a hinge insert configured to engage said hinge receptacle; and a catch insert configured to lock onto the catch receptacle upon rotation of the mechanical interface unit about the hinge axis while the hinge insert engages the hinge receptacle, so as to bring the tube into engagement with the peristaltic mechanism.

2. The system of claim 1, further comprising a door configured to prevent axial motion of the tube.

3. The system of claim 1, wherein said key structure is embedded on said catch receptacle.

4. The system of claim 1, wherein said peristaltic pump includes multiple fingers.

5. The system of claim 1, wherein said key is fixed to said body.

6. The system of claim 5, wherein said body encases said catch receptacle and said peristaltic pump.

7. The system of claim 1, further comprising a rim surrounding the peristaltic mechanism.

8. The system of claim 7, further comprising a door, configured to close over the rim so as to enclose the peristaltic mechanism and to prevent unintentional detachment of the mechanical interface unit from the pump body.

9. The system of claim 8, wherein said rim comprises openings shaped to receive the tube so that the tube extends through the openings when said door is closed.

* * * * *